US012310717B2

(12) United States Patent
Wu et al.

(10) Patent No.: US 12,310,717 B2
(45) Date of Patent: May 27, 2025

(54) GAIT ANALYSIS SYSTEM

(71) Applicant: Regeneron Pharmaceuticals, Inc., Tarrytown, NY (US)

(72) Inventors: Xuefang Wu, Hopkinton, MA (US); Rinol Alaj, Jersey City, NJ (US); Sara Hamon, Darien, CT (US); Matthew F. Wipperman, Brooklyn, NY (US); Olivier Harari, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 90 days.

(21) Appl. No.: 17/326,619

(22) Filed: May 21, 2021

(65) Prior Publication Data

US 2021/0369141 A1 Dec. 2, 2021

Related U.S. Application Data

(60) Provisional application No. 63/054,007, filed on Jul. 20, 2020, provisional application No. 63/030,006, filed on May 26, 2020.

(51) Int. Cl.
*A61B 5/11* (2006.01)
*A61B 5/00* (2006.01)
*A61B 5/22* (2006.01)

(52) U.S. Cl.
CPC ............... *A61B 5/112* (2013.01); *A61B 5/22* (2013.01); *A61B 5/4836* (2013.01);
(Continued)

(58) Field of Classification Search
None
See application file for complete search history.

(56) References Cited

U.S. PATENT DOCUMENTS 3,850,034 A 11/1974 Tsuchiya et al.
9,307,932 B2 4/2016 Mariani et al.
(Continued)

FOREIGN PATENT DOCUMENTS

RU 71 518 U1 3/2008
RU 2021 101 344 A 8/2022

OTHER PUBLICATIONS

Baker "The Gait Profile Score and Movement Analysis Profile" Published by Science Direct, Oct. 2009, pp. 1-9 (Year: 2009).*
(Continued)

*Primary Examiner* — Devin B Henson
*Assistant Examiner* — Matthew Eric Ogles
(74) *Attorney, Agent, or Firm* — Bookoff McAndrews, PLLC

(57) ABSTRACT

A gait analysis system is disclosed. Some implementations of the gait analysis system include instrumented footwear including mobile sensors, a processor, a computer-readable data storage device storing program instructions. The program instructions can control the system to perform operations, including, determining gait information of a user performing a test routine, using the instrumented footwear. The operations can also include determining gait parameters based on the gait information. The operations can also include determining gait symmetry of the user based on the gait parameters. The operations can also include determining a gait signature of the user based on the gait parameters. The operations can also include determining a treatment effect based on the gait signature.

19 Claims, 14 Drawing Sheets

(52) U.S. Cl.
CPC .... *A61B 5/6807* (2013.01); *A61B 2562/0219* (2013.01); *A61B 2562/0247* (2013.01)

(56) References Cited

U.S. PATENT DOCUMENTS

| | | |
|---|---|---|
| 9,591,998 B2 | 3/2017 | Wilson et al. |
| 10,405,779 B2 | 9/2019 | Merrell et al. |
| 2004/0143452 A1* | 7/2004 | Pattillo ................ A61B 5/1038 600/595 |
| 2010/0324455 A1 | 12/2010 | Rangel et al. |
| 2016/0370854 A1* | 12/2016 | Steele ..................... G06F 3/011 |
| 2017/0000383 A1* | 1/2017 | Brown ................ A61B 5/4023 |
| 2018/0092572 A1 | 4/2018 | Sanchez et al. |
| 2019/0298226 A1 | 10/2019 | Filipowicz |
| 2020/0000373 A1* | 1/2020 | Agrawal ............. A61B 5/7405 |
| 2020/0147451 A1 | 5/2020 | Frank et al. |
| 2022/0061698 A1* | 3/2022 | Melakessou ......... A61B 5/1038 |

OTHER PUBLICATIONS

International Search Report, International Appplication No. PCT/US2021/033558, International Filing Date May 21, 2021, Date of Mailing Sep. 14, 2021.

Moticon ReGo AG, "Total Force Validation Study: Moticon Science Sensor Insole (insole3)", Copyright (c) 2020 (24 pages).

* cited by examiner

| Center of Pressure (COP) | | |
|---|---|---|
| Mean gait line length (left) | mm | Length of the average gait line (left foot) |
| Mean gait line length (right) | mm | Length of the average gait line (right foot) |
| Mean gait line width (left) | mm | Width of the average gait line (left foot) |
| Mean gait line width (right) | mm | Width of the average gait line (right foot) |
| Mean COP (AP/ML) in x direction (left) | mm | Mean of center of pressure in x direction (left foot) |
| Mean COP (AP/ML) in y direction (left) | mm | Mean of center of pressure in y direction (left foot) |
| Mean COP (AP/ML) in x direction (right) | mm | Mean of center of pressure in x direction (right foot) |
| Mean COP (AP/ML) in y direction (right) | mm | Mean of center of pressure in y direction (right foot) |
| SD COP (AP/ML) in x direction (left) | mm | Standard deviation of center of pressure in x direction (left foot) |
| SD COP (AP/ML) in y direction (left) | mm | Standard deviation of center of pressure in y direction (left foot) |
| SD COP (AP/ML) in x direction (right) | mm | Standard deviation of center of pressure in x direction (right foot) |
| SD COP (AP/ML) in y direction (right) | mm | Standard deviation of center of pressure in y direction (right foot) |
| Length of Bounding box of COP (AP/ML)(left) | mm | Length of the box just containing all COP points (left foot) |
| Width of Bounding box of COP (AP/ML)(left) | mm | Width of the box just containing all COP points (left foot) |
| Length of Bounding box of COP (AP/ML)(right) | mm | Length of the box just containing all COP points (right foot) |
| Width of Bounding box of COP (AP/ML)(right) | mm | Width of the box just containing all COP points (right foot) |
| Mean COP velocity (left) | mm/s | Mean velocity of the COP travelling across the sensor insole surface (left foot) |
| Mean COP velocity (right) | mm/s | Mean velocity of the COP travelling across the sensor insole surface (right foot) |
| COP trace length (left) | mm | Overall travel of the COP across the sensor insole surface (left foot) |
| COP trace length (right) | mm | Overall travel of the COP across the sensor insole surface (right foot) |

FIG. 5A

| Ground Reaction Force (GRF) | | |
|---|---|---|
| Mean total force during stance phase (left) | N | Mean force of all steps (left foot) |
| Mean total force during stance phase (right) | N | Mean force of all steps (right foot) |
| Maximum total force during stance phase (left) | N | Maximum force of all steps (left foot) |
| Maximum total force during stance phase (right) | N | Maximum force of all steps (right foot) |
| Mean of all maxima of total force during all stance phase (left) | N | Averages of maximum total force of all steps (left foot) |
| Mean of all maxima of total force during all stance phase (right) | N | Averages of maximum total force of all steps (right foot) |
| Temporal parameters | | |
| Mean gait cycle time | s | Time from the one help strike to the next heel strike of the same foot, averaged over all steps |
| Mean gait cadence | Strides/min | Number of strides per minute |
| Mean double support time | s | Mean double support time, relative to the mean gait cycle time |
| Mean fraction of double support | % | Mean double support time, relative to the mean gait cycle time |
| Mean double support time (left) | s | Side-specific double support time(left), with the left mean double support time considering the time starting from the right foot's heel strike to the left foot's toe off (and vice versa) |
| Mean double support time (right) | s | Side-specific double support time(right), with the right mean double support time considering the time starting from the left foot's heel strike to the right foot's toe off (and vice versa) |
| Mean step duration (left) | s | Average time between consecutive heel strike of the left foot |
| Mean step duration (right) | s | Average time between consecutive heel strike of the right foot |
| Mean stance duration (left) | s | Time from heel strike to toe off (of left foot side), averaged over all steps |
| Mean stance duration (right) | s | Time from heel strike to toe off (of right foot side), averaged over all steps |

FIG. 5B

| Temporal parameters | | |
|---|---|---|
| SD stance duration (left) | s | Standard deviation of duration of stance phase (left foot) |
| SD stance duration (right) | s | Standard deviation of duration of stance phase (right foot) |
| Mean swing duration (left) | s | Time from toe off to heel strike (of left foot side), averaged over all steps |
| Mean swing duration (right) | s | Time from toe off to heel strike (of right foot side), averaged over all steps |
| SD swing duration (left) | s | Standard deviation of duration of swing phase (left foot) |
| SD swing duration (right) | s | Standard deviation of duration of swing phase (right foot) |
| Mean fraction of stance phase (left) | % | Mean stance duration, relative to the mean gait cycle time (left foot) |
| Mean fraction of stance phase (right) | % | Mean stance duration, relative to the mean gait cycle time (right foot) |
| SD fraction of stance phase (left) | % | Standard deviation of fraction of stance phase (left foot) |
| SD fraction of stance phase (right) | % | Standard deviation of fraction of stance phase (right foot) |
| Mean fraction of swing duration (left) | % | Mean swing duration, relative to the mean gait cycle time (left foot) |
| Mean fraction of swing duration (right) | % | Mean swing duration, relative to the mean gait cycle time (right foot) |
| SD fraction of swing duration (left) | % | Standard deviation of fraction of swing phase (left foot) |
| SD fraction of swing duration (right) | % | Standard deviation of fraction of swing phase (right foot) |
| Force raise (left) | s | Time to first force peak after initial ground contact (left foot) |
| Force raise (right) | s | Time to first force peak after initial ground contact (right foot) |
| Takeoff Dynamics (left) | 1 | Ratio of force value of force minimum in stance phase and 2nd force peak (takeoff) (left foot) |
| Takeoff Dynamics (right) | 1 | Ratio of force value of force minimum in stance phase and 2nd force peak (takeoff) (right foot) |
| Gait direction dynamics (left) | g | Amplitude of foot acceleration in direction of walking (left foot) |
| Gait direction dynamics (right) | g | Amplitude of foot acceleration in direction of walking (right foot) |
| Spatial parameters | | |
| Mean stride length | m | The displacement of the same foot in walking direction. This parameter is the mean over all detected steps. The mean is determined from left and right data, separately, and finally averaged over left and right |
| Foot flexibility (left) | g | Amplitude of foot acceleration in body's vertical direction (left foot) |
| Foot flexibility (right) | g | Amplitude of foot acceleration in body's vertical direction (right foot) |
| Walking distance | m | The walking distance traveled over the entire measurement |
| Mean walking speed | m/s | The mean stride length divided by the mean gait cycle time. |

FIG. 5C

GAIT ANALYSIS SYSTEM

CROSS-REFERENCES TO RELATED APPLICATIONS

This application claims priority to U.S. Provisional Application No. 63/030,006, filed May 26, 2020, and U.S. Provisional Application No. 63/054,007, filed Jul. 20, 2020, the contents of each of which are incorporated herein by reference in their entireties.

BACKGROUND

Gait disorders can result from a wide variety of injuries, diseases, and other ailments. Currently, tests used to diagnose gait disorders often involve simple functional assessments. However, data collected from such tests is subjective and does not provide sufficient information to assess the relative severity of afflictions. In some cases, a clinical laboratory may perform gait evaluations. However, the high cost and complexity of laboratory-grade sensors systems may limit their size. As such, they may not allow evaluation of gaits over a substantial distance.

SUMMARY

The following presents a simplified summary of the disclosed subject matter in order to provide a basic understanding of some aspects of the disclosed subject matter. This summary is not intended to identify key or critical elements of the disclosed subject matter or delineate the scope of the claimed subject matter.

The present disclosure provides gait analysis systems and methods. In some implementations, a gait analysis system includes instrumented footwear including one or more mobile sensors, a processor, a computer-readable data storage device storing program instructions. The program instructions, when executed by the processor, can control the system to perform operations, including, determining, using the instrumented footwear, gait information of a user performing a test routine. The operations can also include determining gait parameters based on the gait information. The operations can also include determining gait symmetry of the user based on the gait parameters. The operations can also include determining a gait signature of the user based on the gait parameters. The operations can also include determining a treatment effect based on the gait signature.

DRAWINGS

FIGS. 5A, 5B, and 5C show gait parameters in accordance with aspects of the present disclosure.

Figure 6A:
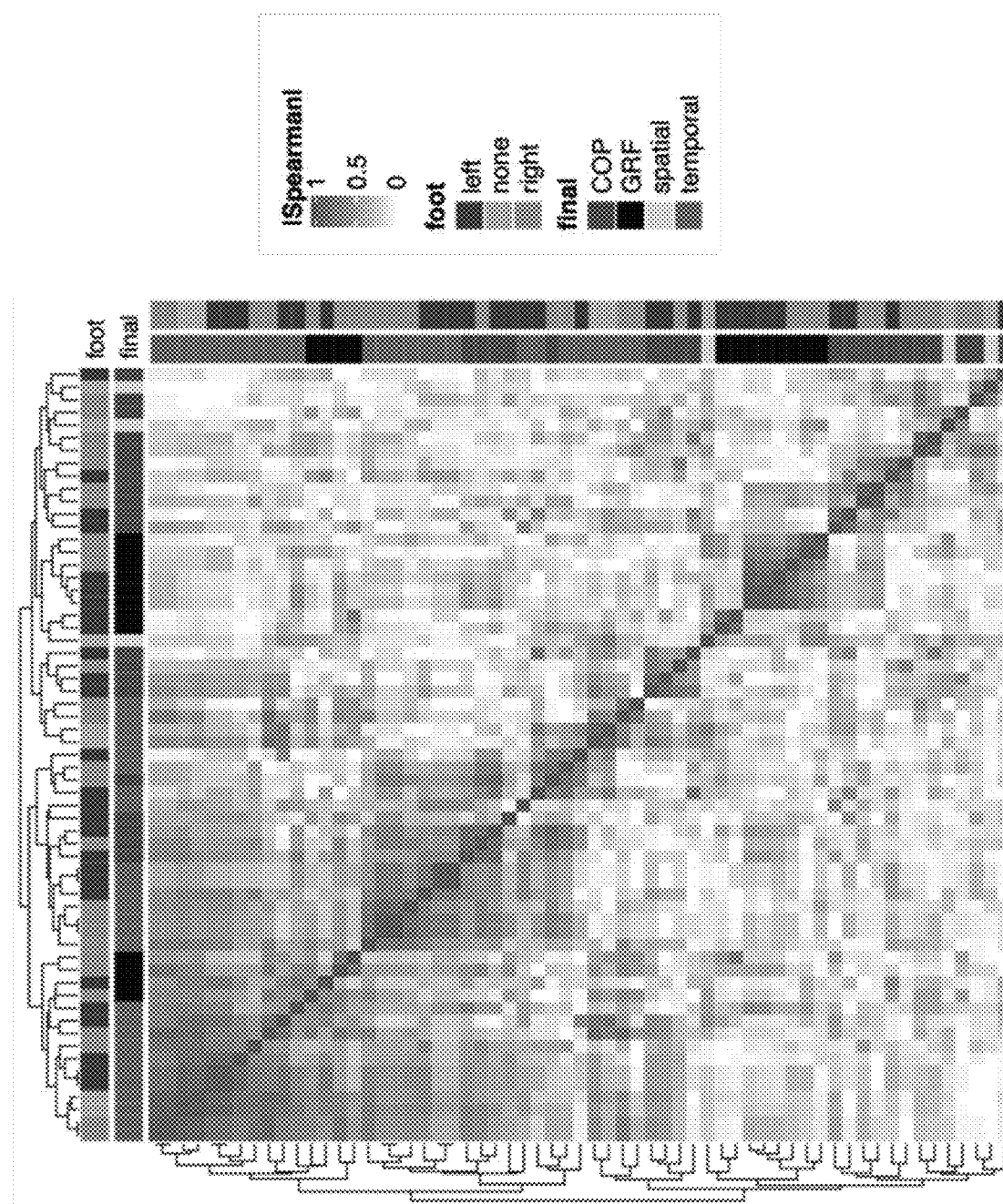
Figure 6B:
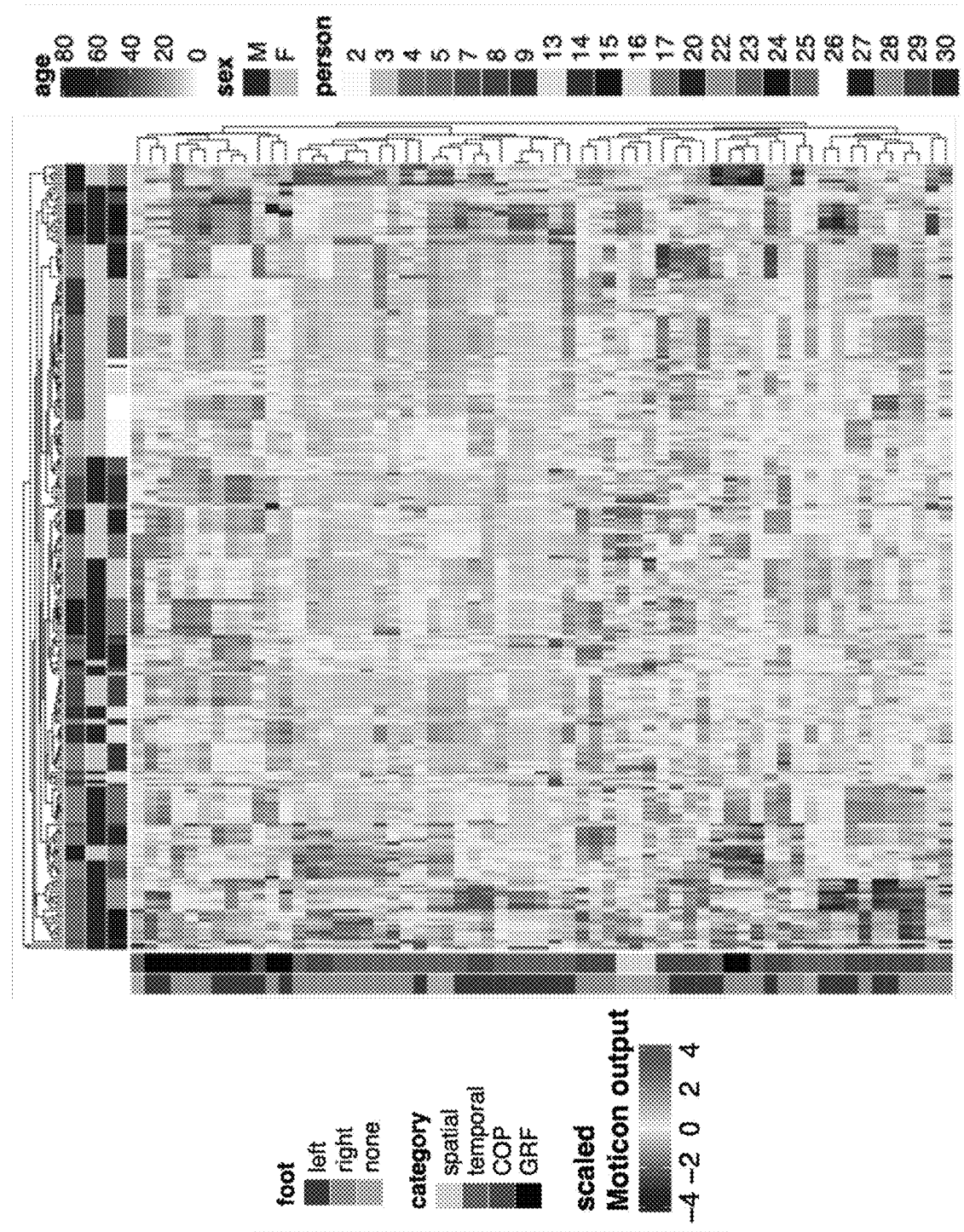
Figure 6C:
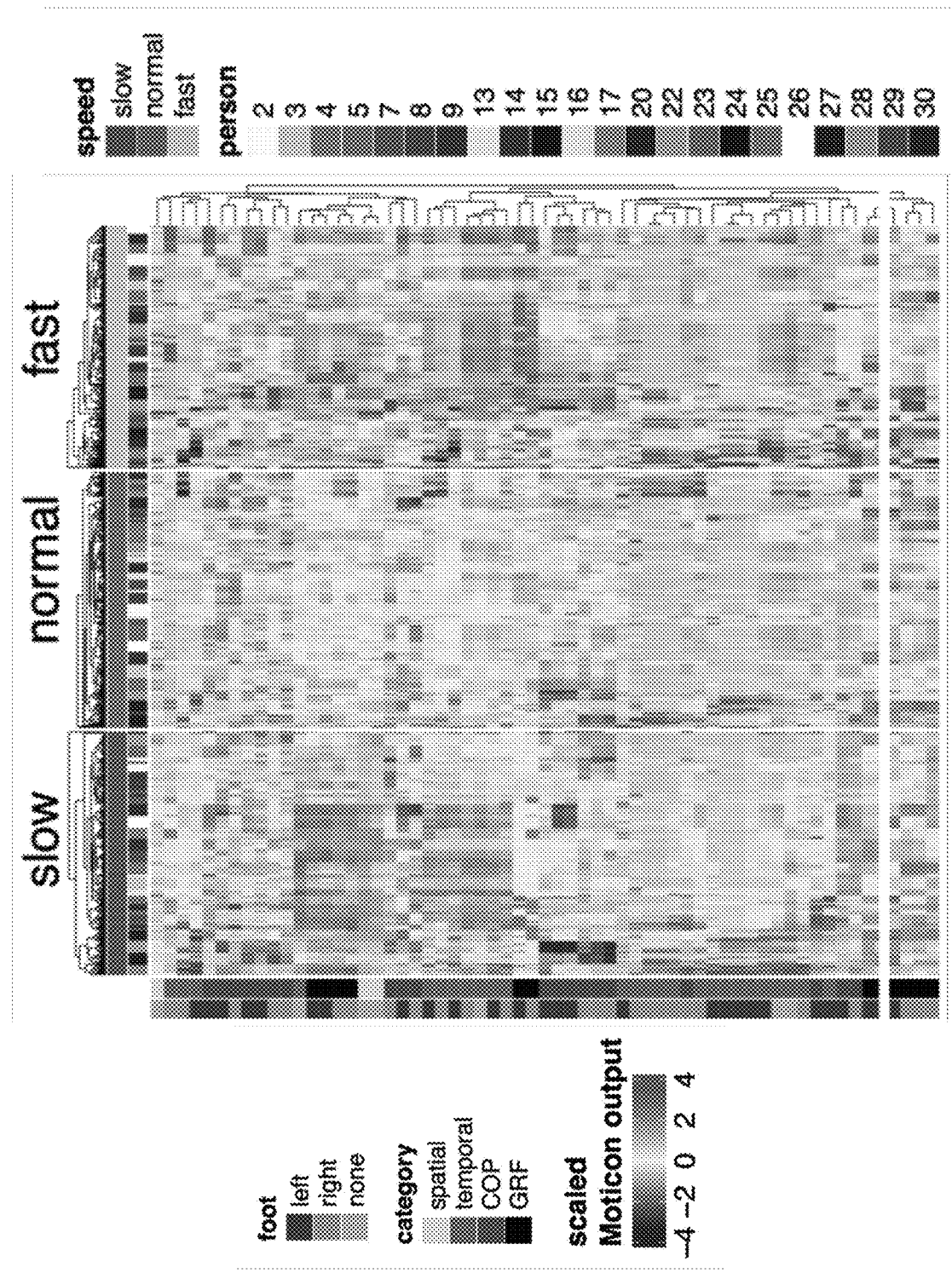

FIGS. 6A, 6B, and 6C show heat maps illustrating correlations between gait parameters in accordance with aspects of the present disclosure.

DETAILED DESCRIPTION

The present disclosure relates to gait evaluation. More specifically, the present disclosure relates to evaluating gaits and determining treatment effects based on the gait evaluations. Treatment effects are relative improvements in an individual's gait resulting from treatment of an affliction in comparison to a reference gait. Implementations of systems and methods disclosed herein generate gait information over a several strides using wearable sensors, determine gait parameters based on the gait information, determine gait signatures based on the gait parameters, and determine effectiveness of treatments based on the gait signatures and gait parameters.

Reference will now be made to specific implementations illustrated in the accompanying drawings. In the following detailed description, numerous specific details are set forth to provide a thorough understanding of the disclosed implementations. However, it will be apparent to one of ordinary skill in the art that implementations may be practiced without these specific details. In other instances, well-known methods, procedures, components, circuits, and networks have not been described in detail so as not to unnecessarily obscure aspects of the implementations.

Figure 1A:
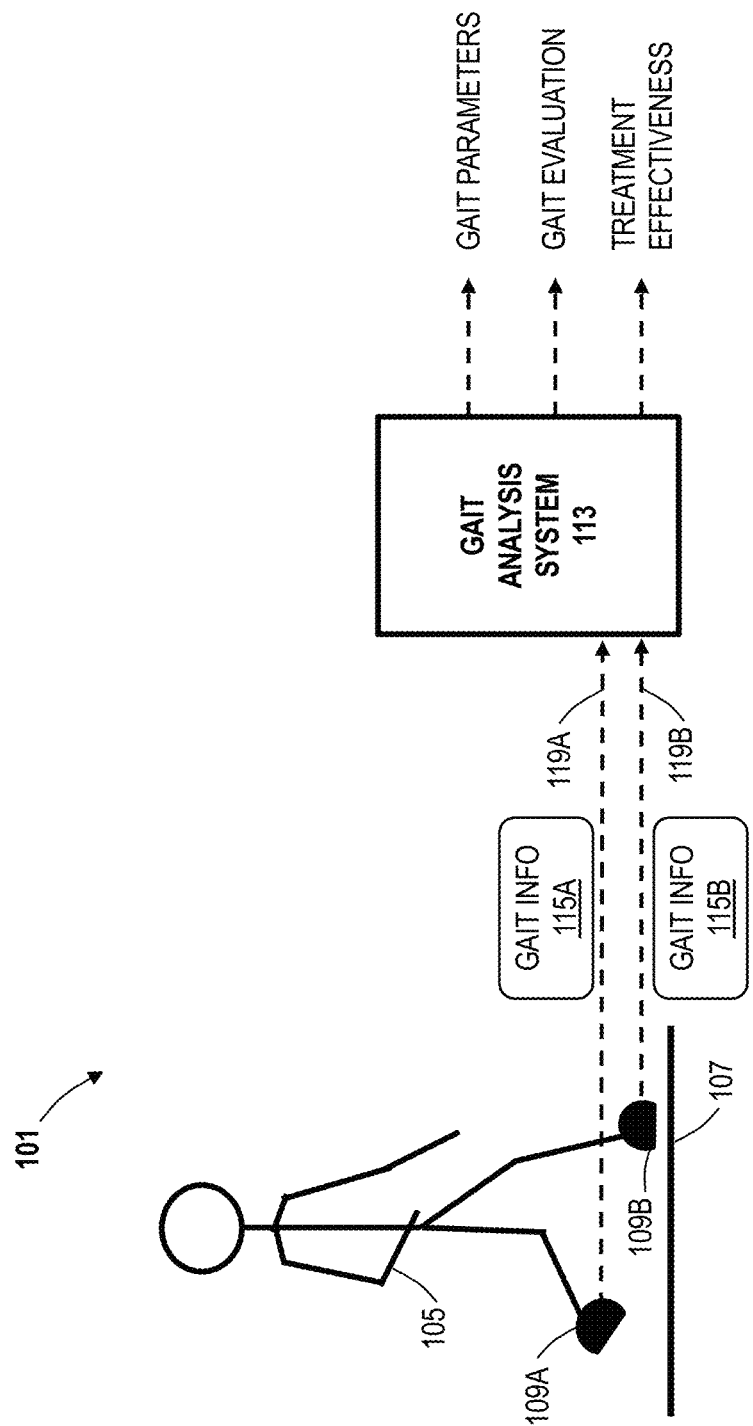
FIG. 1A shows a block diagram illustrating an exemplary environment for implementing systems and methods in accordance with aspects of the present disclosure.

FIG. 1A shows a system block diagram illustrating an example environment 101 for implementing systems and methods in accordance with aspects of the present disclosure. The environment 101 includes a user 105 traversing the ground 107 on foot while wearing instrumented footwear 109A and 109B. The instrumented footwear 109A and 109B generates respective gait information 115A and 115B and provides it to the gait analysis system 113 using one or more communication links 119A and 119B. For example, the gait analysis system 113 can receive the gait information 115A, 115B from the instrumented footwear 109A, 109B while the user 105 performs a test routine involving walking, running, and standing.

The user 105 can be any individual. In some implementations, the user 105 can be an individual having an affliction that affects the individual's 105 gait for which the user 105 may be receiving treatment, such as physical therapy. The afflictions can be, for example, damage, deterioration, or malformation of the individual's 105 musculoskeletal or neurological systems that cause asymmetries in the user's 105 stride. For example, nerve damage from a herniated disk in the user's spine may cause the user 105 to favor one foot over the other. Additionally, in some implementations, the user 105 can be an unafflicted individual lacking or substantially lacking any gait-affecting ailments. The user 105 can generate reference gait information 115A, 115B representing an unafflicted stride.

The instrumented footwear 109A, 109B can be a pair of instrumented shoes, insoles, socks, or other foot covering wearable by the user 105. The instrumented footwear 109A, 109B can comprise mobile sensors, including accelerometers, gyroscope, pressure sensors and force transducers. The instrumented footwear 109A, 109B can also include a processor, a computer-readable memory, and a data communication device. In some implementations, the processor, the computer-readable memory, and the data communication device are provided by an application-specific integrated circuit (ASIC) that amplifies, conditions, normalizes, and combines signals output by the sensors to generate gait information 115A, 115B, which the processor communicates to the gait analysis system 113 using the data communication device via the communication links 119A, 119B. In some implementations, the instrumented footwear 109A, 109B can be MOTICON SCIENCE INSOLES by MOTICON REGO AG, DE.

The gait analysis system 113 can be one or more computing devices that analyze the gait information 115 to determine gait parameters. Using the gait parameters, the gait analysis system 113 can evaluate the user's 105 gait. Additionally, based on the gait parameters and gait analysis, the gait analysis system 113 can determine the effectiveness of treatments the user 105 may be undergoing. For example, the gait analysis system 113 can compare the user's 105 current gait parameters to their past gait parameters and other reference information to identify improvements in performance.

The communication links 119A, 119B can be any wired links, wireless links, or combination thereof that use any combination of one or more types of transmission techniques and protocols. For example, the communication links 119A and 119B can use the BLUETOOTH® wireless communication protocol. In some implementations the instrumented footwear 109A and 109B can stream the information to the gait analysis system 113 via the communication links 119A, 119B. In some other implementations, the instrumented footwear 109A and 109B can bundle and transmit the gait information 115A, 115B via the communication links 119A, 119B after completion of a test routine.

Figure 1B:
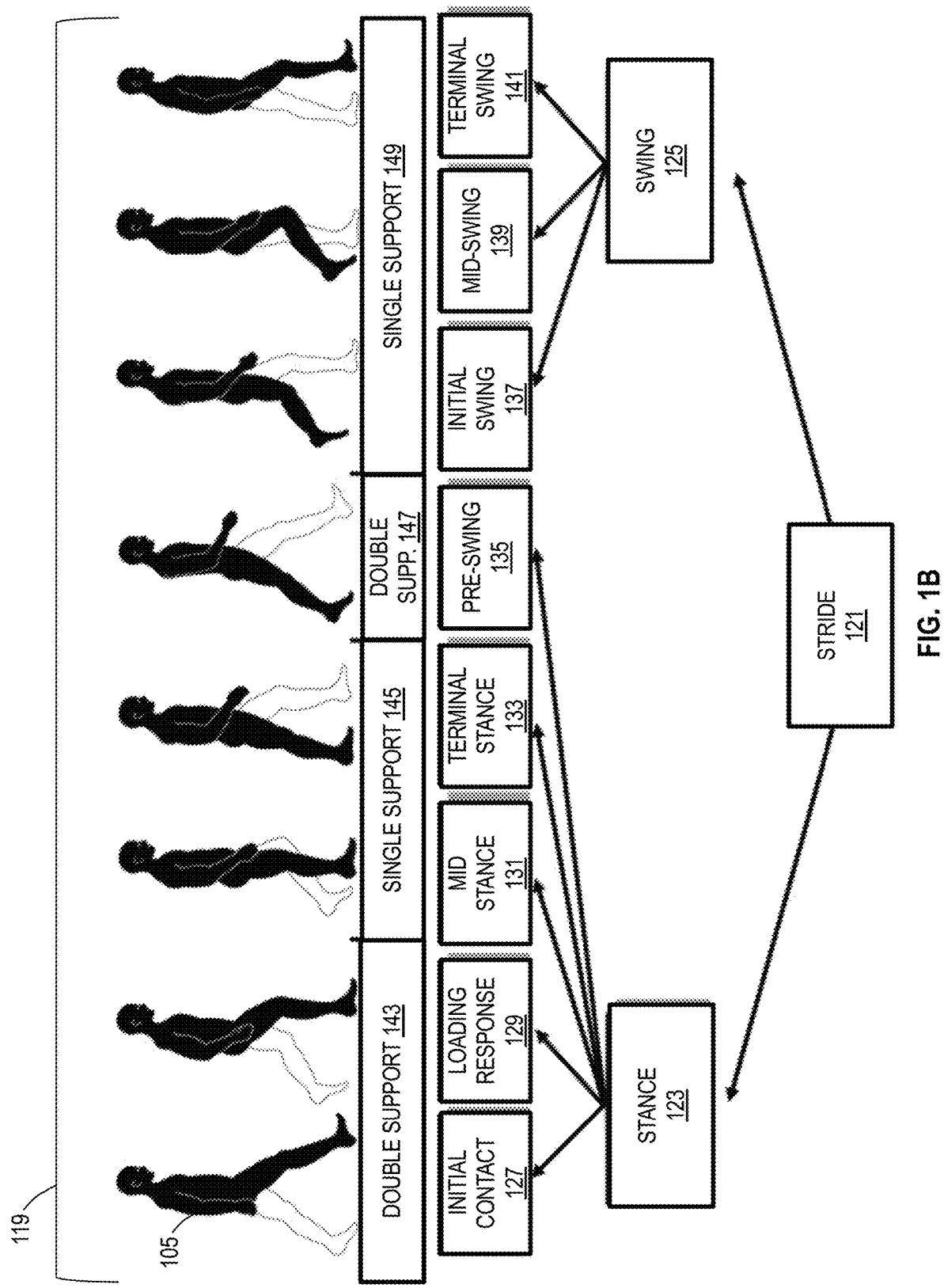
FIG. 1B shows elements of a stride determined by systems and methods in accordance with aspects of the present disclosure.

FIG. 1B shows elements of a stride 121 of the user 105 measurable over a distance 119 by systems and methods in accordance with aspects of the present disclosure. The stride 121 includes a stance phase 123 and a swing phase 125. The components of the stance phase 123 can include an initial contact 127, a loading response 129, a mid-stance 131, a terminal stance 133, and a pre-swing 135. The components of the swing phase 125 can include an initial swing 137, a mid-swing 139, and a terminal swing 141. Further, the initial contact 127, the loading response 129, can be a first combination in which both of the user's 105 feet contact the ground, which is referred to as a double support movement 143. The mid-stance 131 and the terminal stance 133 can be a second combination in which only one of the user's 105 feet contact the ground, which is referred to as single support movement 134. The pre-swing 135 can be a second double support movement 147. The initial swing 137, the mid-swing 139, and the terminal swing 141 can be a second single support movement 149. While FIG. 1B shows a single stride 121 over the distance 119, it is understood that systems and methods consistent with those disclosed herein can involve gait evaluation routines including two or more strides over greater distances.

Figure 1C:
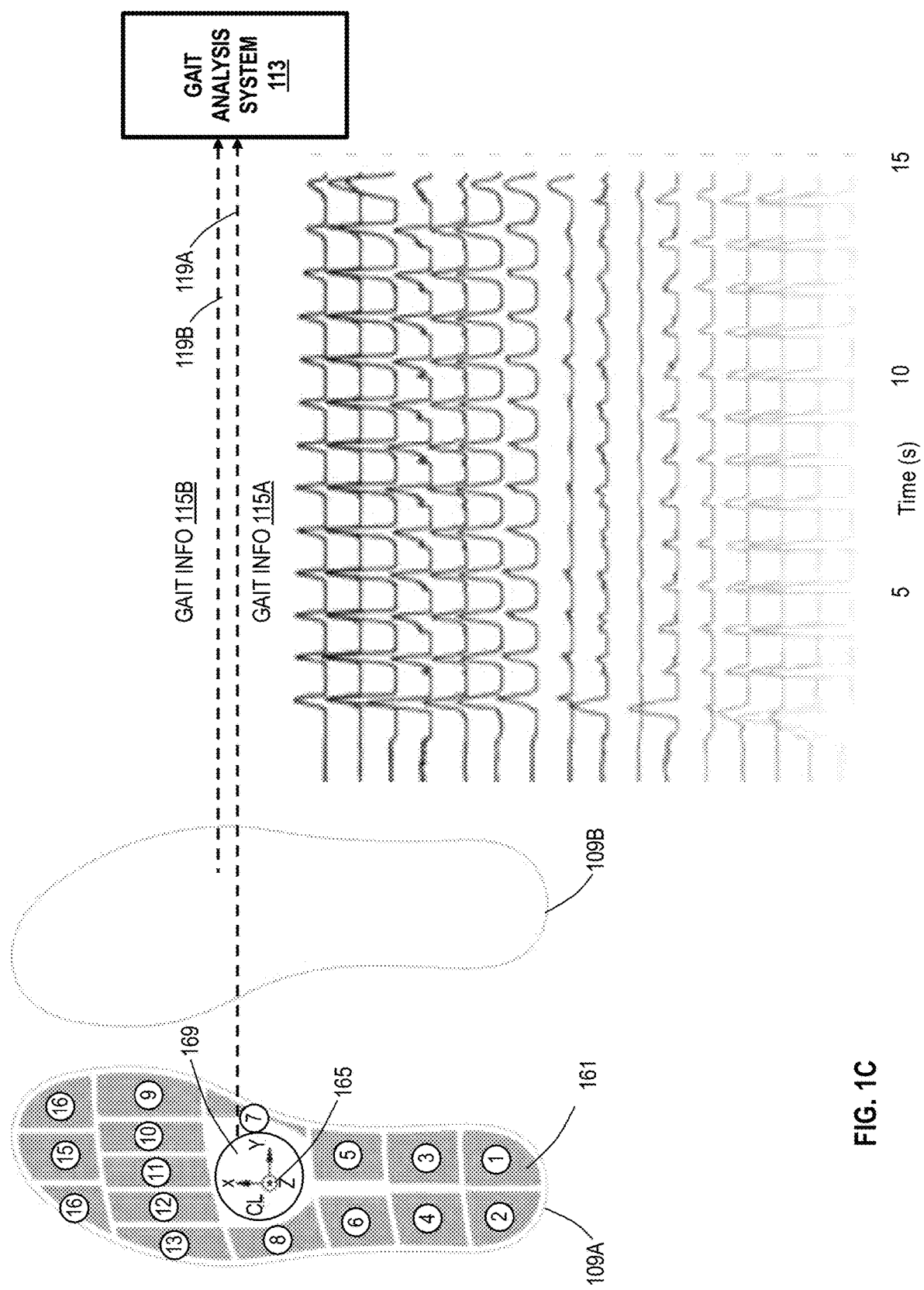
FIG. 1C shows gait information provided by instrumented footwear to a gait analysis system in accordance with aspects of the present disclosure.

FIG. 1C shows gait information 115A, 115B provided by the instrumented footwear 109A or 109B to the gait analysis system 113 through the communication link 119A, 119B in accordance with aspects of the present disclosure. In some implementations, the instrumented footwear 109A, 109B includes force sensors 116 and an accelerometer 165. For example, the force sensors 161 can measure vertical pressure applied between the user's 105 foot and ground. Additionally, in some implementations, the force sensors 161 can be distributed on over the area of the instrumented footwear 109A, 109B. As illustrated in the example shown in FIG. 1C, the instrumented footwear 109A, 109B can include 16 force sensors 161 substantially distributed over the entire surface area of the instrumented footwear 109A, 109B. In some implementations, the force sensors 161 are grouped at contact points corresponding to the balls and heel of the user's feet. In some implementations, the force sensors 161 are distributed over substantially over the entire area of the instrumented footwear 109A, 109B with increased density at the contact points corresponding to the balls and heel.

Additionally, the instrumented footwear 109A, 109B can include one or more accelerometers 165 that output data indicating acceleration in one or more axes. In some implementations, the accelerometer 165 is a multi-axis (vertical, X-axis), horizontal, Y-axis), and elevation, Z-axis) accelerometer that can measure acceleration in six degrees of freedom (forward translation (+X-axis), backward translation (−X-axis), right (+Y-axis), left (−Y-axis), up (+Z-axis), down (−Z-axis), pitch (rotation around X-axis), roll (rotation around Y-axis), and yaw (rotation around Z-axis). For example, the accelerometer 165 measurement unit can be a three-dimensional gyroscope.

Further, the footwear 109A, 109B can include controllers 169, including respective microprocessors, data input/output (I/O) circuits, data conditioning circuits, and transmitters (not shown). In some implementations, the controllers 169 can also include the accelerometers 165. The controllers 169 collect data from the force sensors 161 and accelerometers 165 via the digital I/O circuits at a rate between about 30 hertz and about 120 hertz. Additionally, the controllers 169 can include hardware, software, or a combination thereof that amplifies, conditions, and processes data from the force sensors 161 and accelerometers 165 to determine the gait information 115A, 115B. Further, the controller 169 can transmits the gait information 115A, 115B using the transmitter via the communication links 119A, 119B. While FIG. 1C only illustrates gait information 115A and elements of instrumented footwear 109A, including force sensors 161, accelerometer 165, and controller 169, it is understood the instrumented footwear 109B can include the same or similar sensors producing substantially the same or similar gait information 115B.

The gait information 115A, 115B can include, for example, information representing a total ground reaction force, which can be the sum of the outputs of the force sensors 161 multiplied by the respective surface area of the force sensors 161. Additionally, the controller 169 can determine respective centers of pressure for the instrumented footwear 109A, 109B. Further, the controller 169 can determine respective heel strike (initial contact) and toe off (stance termination) events timepoint are determined from total force, individual force, center of pressure and acceleration along anterior-posterior direction. Other data determined by the controller 169 can include, pressure applied on each pressure sensor, 3D acceleration, and 3D angular velocity.

Figure 1D:
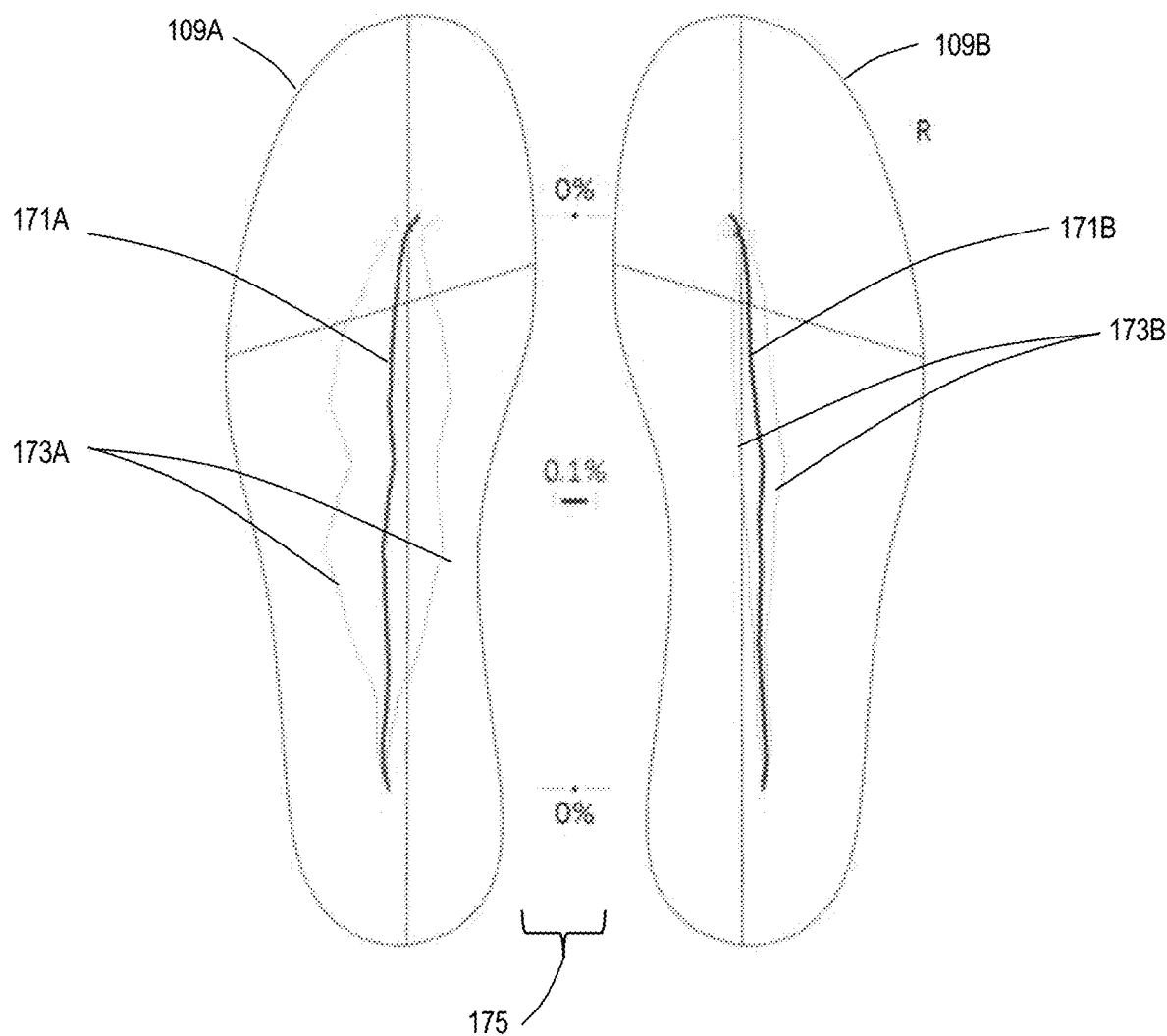
FIG. 1D shows gait parameters in relation to instrumented footwear in accordance with aspects of the present disclosure.

FIG. 1D illustrates an example of gait lines 171A and 171B determined by the gait analysis system 113 based on the gait information 115A and 115B from the instrumented footwear 109A and 109B. A gait line represents the translational movement of the center of pressure (COP) during the stance phase (e.g. stance 123) of a stride (e.g., stride 121). The gait lines 171A, 171B represent the average gait line of steps taken during a test walk. Gait deviation lines 173A and 173B represent the standard deviation of the gait lines 171A, 171B in a medio-lateral direction over the walk. The differences between the left and right foot are indicated by visual lines and percentage values 175. The percentage values are with respect to the insole length and width. For example, FIG. 1D illustrates a 1% difference between the left and the right foot in a medio-lateral direction at a central portion of the foot. In some implementations, the gait lines 171A, 171B are computed for individual steps during a test routine. The gait lines 171A, 171B and other gait information can be determined using timing, balance, pressure, force, and motion information obtained from the instrumented footwear 109A and 109B.

Figure 1E:
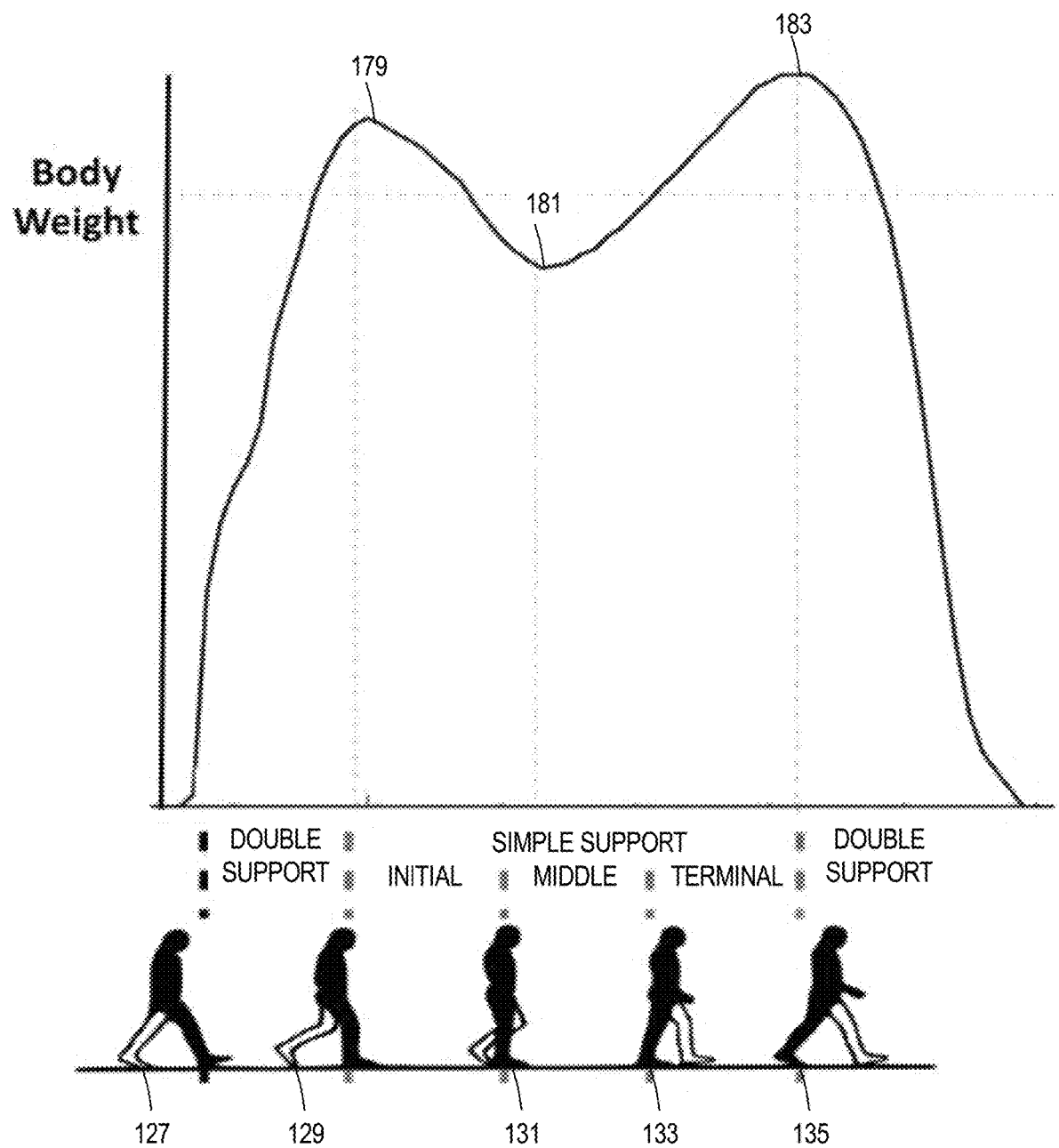
FIG. 1E shows gait parameters in relation to gait phases in accordance with aspects of the present disclosure.

FIG. 1E illustrates an example of gait parameters corresponding to components of a stride (e.g., stride 121) determined by the gait analysis system 113 for one of user's feet based on force information (e.g., gait information 115A and 115B) from instrumented footwear (e.g., instrumented footwear 109A, 109B). The gait parameters of the stride can include initial contact 127, loading response 129, mid stance 131, terminal stance 133, and pre-swing 135, which can be the same as those described above regarding FIG. 1B. As shown in FIG. 1E, a first peak ground reaction force 179 can occur after heel strike (early stance) occurring during the loading response 129. Additionally, a local minimum force 181 can occur during mid-stance 131 between the loading response 129 and the terminal stance 133. Further, a second peak ground reaction force 183 can occur before toe off (late stance) of the pre-swing 135.

Figure 2:
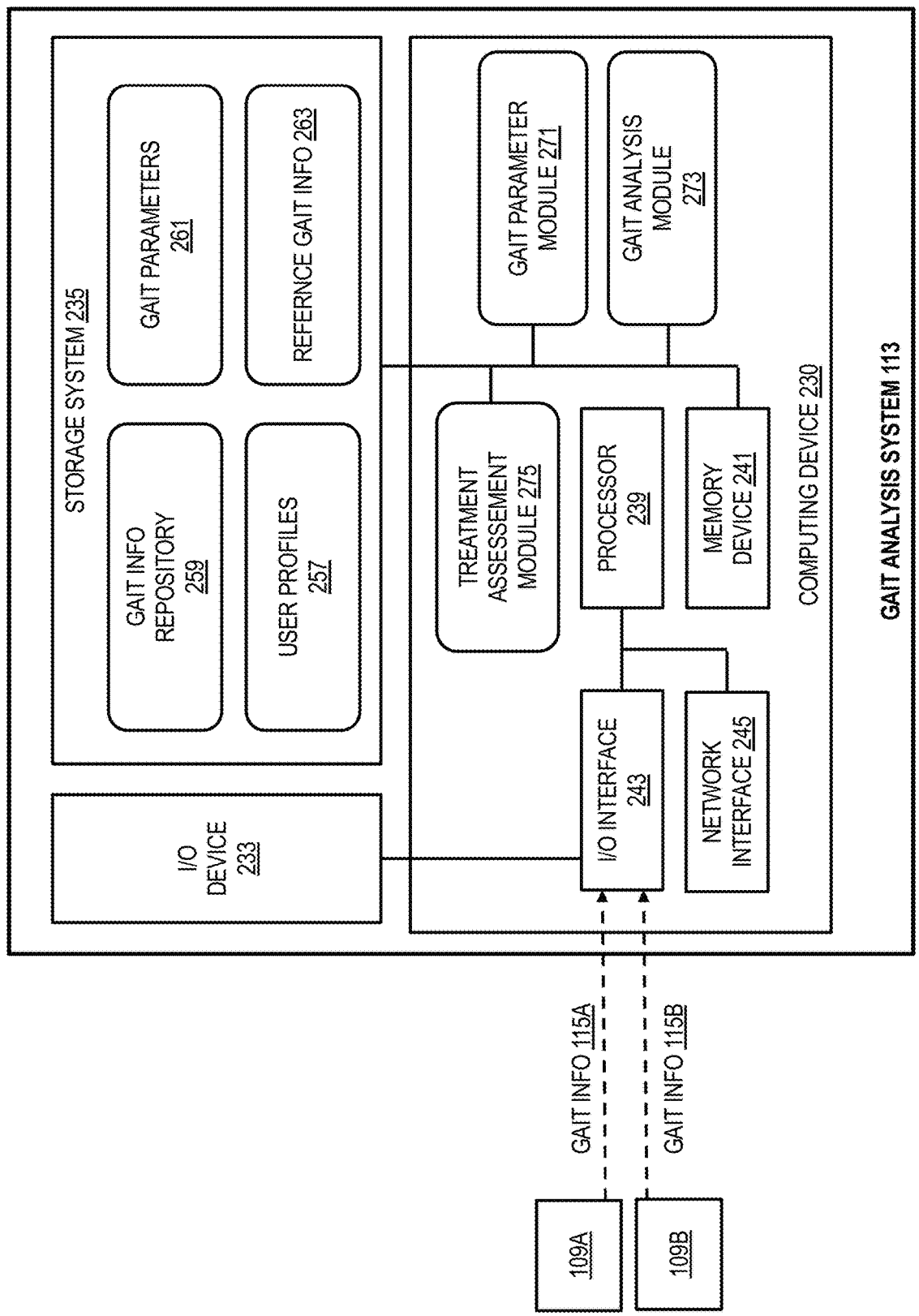
FIG. 2 shows a block diagram illustrating an example of a gait analysis system in accordance with aspects of the present disclosure.

FIG. 2 shows a system block diagram illustrating an example of a gait analysis system 113, which can be the same or similar to that described above. The gait analysis system 113 includes hardware and software that perform the processes and functions disclosed herein. The gait analysis system 113 includes a computing device 230, an input/output (I/O) device 233, and a storage system 235. The I/O device 233 can include any device that enables an individual (e.g., user 103) to interact with the computing device 230 (e.g., a user interface) and/or any device that enables the computing device 230 to communicate with one or more other computing devices using any type of communications link. The I/O device 233 can be, for example, a touchscreen display, pointer device, keyboard, etc.

The storage system 235 can comprise a computer-readable, non-volatile hardware storage device that stores information and program instructions. For example, the storage system 235 can be one or more flash drives and/or hard disk drives. In accordance with aspects of the present disclosure, the storage system 235 can store user profiles 257, a gait information repository 259, gait parameters 261, and reference gait information 263. The user profiles 257 can include information describing individuals (e.g., user 105) for which the gait analysis system 113 has collected gait information 115A, 115B. The user profiles 257 can comprise demographic and physical information of the users, including identification, age, gender, height, weight, body mass index, pains, injuries, and ailments. The gait information repository 259 can store the gait information 115A, 115B generated by the instrumented footwear 109A, 109B. For example, the gait information can include force per time data and acceleration per time data from the instrumented footwear 109A, 109B. The gait parameters 261 can store information generated by the gait analysis system based on information included in the user profiles 257 and the gait information repository 259. In some implementations, the gait parameters 261 can include some or all of the information illustrated in FIGS. 5A, 5B, and 5C. The reference gait information 263 can include information relating gait parameters with reference information of gaits affected by ailments. In some implementations, the reference gait information 263 can characterize particular gait parameters or combinations thereof with ailment conditions. For example, gait reference information 263 define a correspondence between gait parameters indicating the force and asymmetry of a subject's gait with a particular ailment and a severity of the ailment.

In some implementations, the computing device 230 includes one or more processors 239 (e.g., microprocessor, microchip, or application-specific integrated circuit), one or more memory devices 221 (e.g., random-access memory (RAM) and read-only memory (ROM)), one or more I/O interfaces 223, and one or more network interfaces 245. The memory device 221 can include a local memory (e.g., a RAM and a cache memory) employed during execution of program instructions. Additionally, the computing device 230 includes at least one communication channel 232 (e.g., a data bus) by which it communicates with the I/O device 233 and the storage system 235. The processor 239 executes computer program instructions (e.g., an operating system and/or application programs), which can be stored in the memory device 221 and/or storage system 235.

The processor 239 can also execute computer program instructions of a gait parameter module 271, a gait analysis module 273, and a treatment assessment module 275. The gait parameter module 271 can determine information stored in the gait parameters 261 using the gait information 115A, 115B generated by the instrumented footwear 109A, 109B and stored in the gait information repository 259. The gait analysis module 273 can determine correlations between various gait information and gait parameters to characterize users' gaits. For example, the gait analysis module 273 can use Spearman correlations between gait parameters, such as illustrated by the example heatmaps shown in FIGS. 6A, 6B, and 6C. In some implementations, the gait analysis module 273 can determine gait signatures of individual users. The treatment assessment module 275 can determine effectiveness of treatments based on the gait signatures, the gait parameters, the gait information, and the profiles. In some implementations, the treatment assessment module 275 can determine differences between a user's gait signature and reference gait signature stored in gait reference information 263 to assess improvement in a user's gait due to treatment. For example, the treatment assessment module 275 can compare user's gait line, such as shown in FIG. 1D, with a previous gait line, with a reference gait line obtained from afflicted individuals of similar profile (physical and demographic) having a same or similar ailment, and a reference gait line obtained from unafflicted individuals of similar profile.

It is noted that the computing device 230 can comprise any general-purpose computing article of manufacture capable of executing computer program instructions installed thereon (e.g., a personal computer, server, etc.). However, the computing device 230 is only representative of various possible equivalent-computing devices that can perform the processes described herein. To this extent, in implementations, the functionality provided by the computing device 230 can be any combination of general and/or specific purpose hardware and/or computer program instructions. In each implementation, the program instructions and hardware can be created using standard programming and engineering techniques, respectively.

Figure 3:
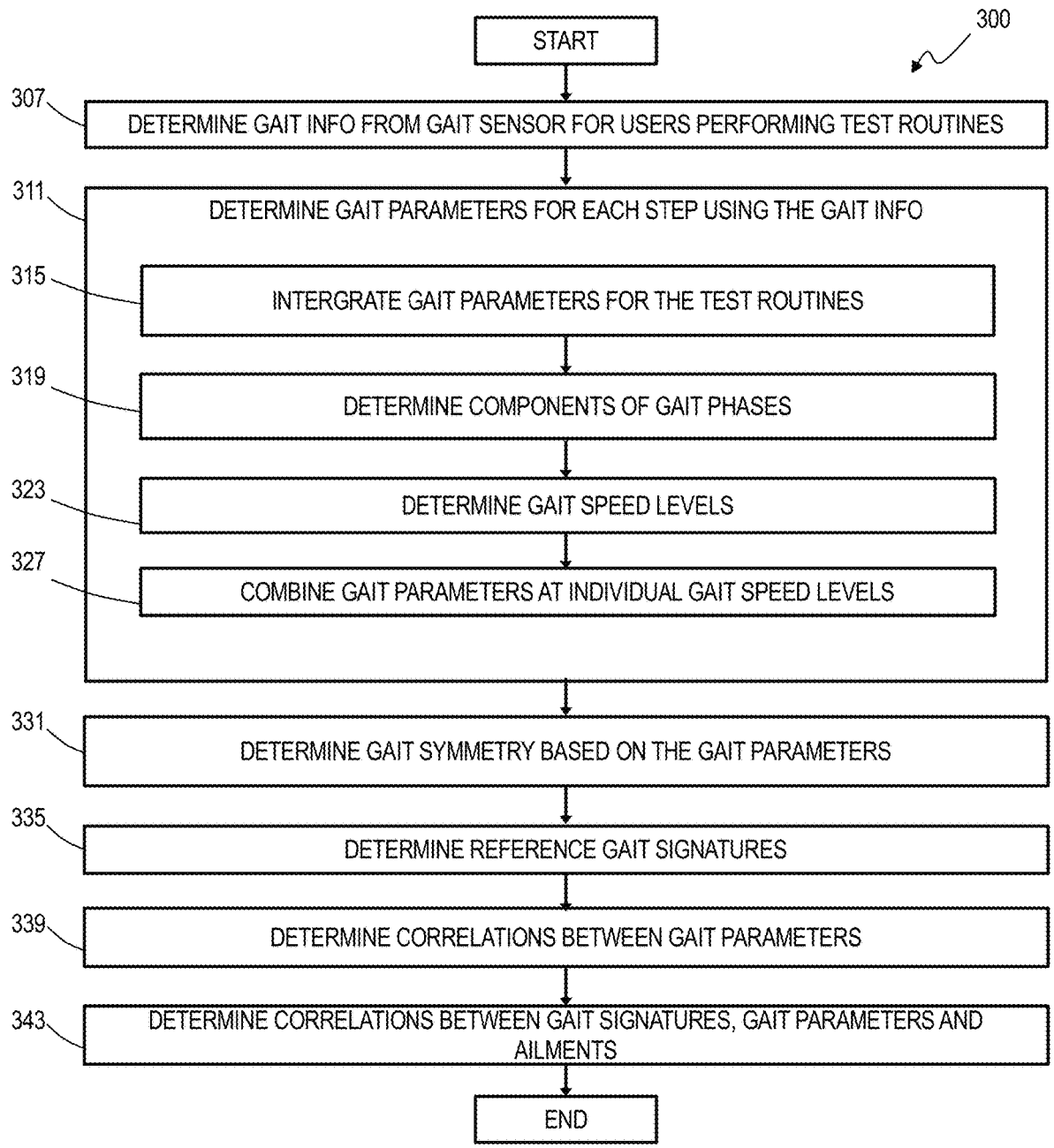
FIG. 3 shows a flow block diagram illustrating an example of a method for determining reference gait information in accordance with aspects of the present disclosure.
Figure 4:
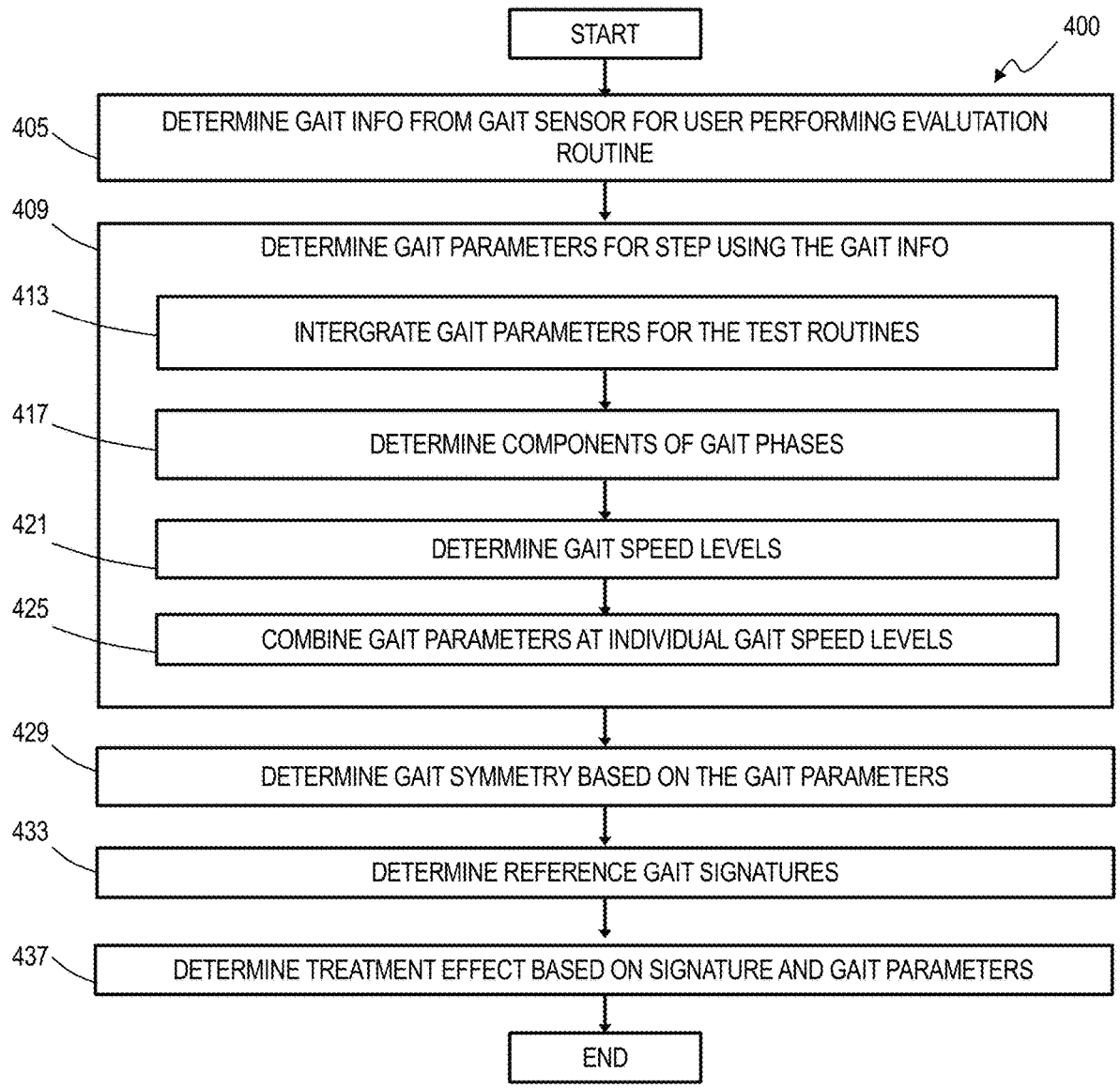
FIG. 4 shows a flow block diagram illustrating an example of a method for evaluating effectiveness of treatments in accordance with aspects of the present disclosure.

The flow diagrams in FIGS. 3 and 4 illustrate examples of the functionality and operation of some implementations of systems, methods, and computer program products according to various implementations consistent with the present disclosure. Each block in the flow diagrams of FIGS. 3 and 4 can represent a module, segment, or portion of program instructions, which includes one or more computer executable instructions for implementing the illustrated functions and operations. In some alternative implementations, the functions and/or operations illustrated in a particular block of the flow diagram can occur out of the order shown in FIGS. 3 and 4. For example, two blocks shown in succession can be executed substantially concurrently, or the blocks can sometimes be executed in the reverse order, depending upon the functionality involved. It will also be noted that each block of the flow diagram and combinations of blocks in the block can be implemented by special purpose hardware-based systems that perform the specified functions or acts, or combinations of special purpose hardware and computer instructions.

FIG. 3 illustrates a method 300 of determining reference gait information (e.g., reference gait information 263) in accordance with some implementations consistent with the present disclosure. At block 307, the method 300 can include determining gait information (e.g., gait information 115A, 115B) of users (e.g., user 105) performing test routines using instrumented footwear (e.g., instrumented footwear 109A, 109B). In some implementations, the users include individuals substantially lacking ailments affecting their gaits. Additionally, in some implementations, the users also include individuals having ailments affecting their gaits. The users can express the ailments in various degrees. For example, the users can have undergone various amounts of treatment and recovery for their ailments. In some implementations, the test routines include walking and standing tests. For example, the test routines can involve testers standing still for about 30 seconds, walking a distance (e.g., distance 119) at a first, comfortable speed, standing still for about a period of time, walking the distance at a second, slow speed, stand still for the period of time, and walking the distance at a third, fast speed. In some implementations, the distance is greater than or equal to about 10 meters and the standing time can be greater than or equal to about 30 seconds.

At block 311, the method 300 determines gait parameters using the gait data collected. at 307. In some implementations, determining the gait parameters includes, at block 315, integrating the gait parameters determined at block 311 from the test routines. In some implementations, integrating includes determining means and standard deviations of the gait parameters over the distance used in the test routine. In some implementations, determining the gait parameters also includes, at block 319, determining components of the gait phases occurring during the test routines using the gait parameters determined at block 311. The components of the gait phases can be the same or similar to those described above. In some implementations, the gait phases include the stance phase (initial contact, loading response, mid stance, terminal stance pre-swing) and the swing phase (initial swing, mid swing, terming swing). In some implementations, determining the gait parameters also includes, at block 325, determining gait speed levels (e.g., slow, comfortable, fast) of the gait parameters determined at block 311. In some implementations, determining the gait parameters also includes, at block 327, combining the gait parameters determined at 311 at the speed levels determined at block 323. In some implementations, the gait parameters can include, for each foot of a user, mean gait line length, mean gait line width, mean center of pressure (X-axis, Y-axis, Z-axis), standard deviation of the center of pressure (X-axis, Y-axis, Z-axis), length of bounding box of the center of pressure, width of bounding box of the center of pressure, mean center of pressure velocity, center of pressure trace length, mean total force during the components of the stance phase, maximum total force during the stance phase, average of all maximum of the total force during the stance phase, mean gait cycle time, mean gait cadence, man double support time, mean fraction of double support, mean step duration, mean stance duration, standard deviation of stance duration, mane swing duration, standard deviation of swing duration, mean fraction of stance phase, standard deviation of stance phase, mean fraction of swing duration, force raise, takeoff dynamics, gait direction dynamics, mean stride length, foot flexibility, walking distance, and mean walking speed. For example, the gait parameters can include some or all of those shown in FIGS. 5A, 5B, and 5C.

At block 331, the method 300 determines gait symmetries based on the gait parameters determined at blocks 311. Gait symmetry can indicate whether a user favored one foot over another. At block 335, the method determines reference gait signatures using the gait parameters determined at 311 and the gait symmetries determined at block 331. At block 339, the method determines correlations between the gait parameters determined at 311. The correlations between gait parameters can be calculated by deriving Spearman correlations between the raw values for the gait parameters. Parameters that cluster together are highly correlative, indicating that they measure very similar trends in the walk. Parameters the have low intraindividual variability measured with intraclass correlation (ICC). In some implementations, between about 5 to about 7 clusters of the 61 raw gait parameters that can be used to describe similar walking trends. These variables often have similar names, or are measuring the same motion bilaterally (left vs right foot), Most parameters in this study have high intraclass correlation (e.g., low intraindividual variability). Endpoints that are summary metrics of multiple parameters control for noise of an individual parameter, so this analysis may help compute these endpoints. Identifying variables with high intraclass correlation helps refine candidate endpoints for comparing clinical groups. This analysis can help inform asymmetry in walking patterns within an individual.

At block 343, the method 300 determines correlations between the gait parameters determined at 311 and the gait symmetries determined at block 331. For example, the system can use linear modeling and principle component analysis (PCA) to determine relationships between the gait parameters and clinical and demographic variables.

FIG. 4 shows a flow block diagram illustrating an example of a method for evaluating effectiveness of treatments in accordance with aspects of the present disclosure. At block 405, the method 400 can include determining gait information (e.g., gait information 115A, 115B) of a user (e.g., user 105) performing an evaluation routine using instrumented footwear (e.g., instrumented footwear 109A, 109B). In some implementations, the user can be a user afflicted with an ailment and who may be receiving treatments for the ailment. In some implementations, the evaluation routine can be the same or similar to the test routine previously described herein regarding FIG. 3, block 307.

At block 409, the method 400 determines gait parameters using the gait data collected. at 405 in a same or similar manner to that previously described herein regarding FIG. 3, block 311. As detailed above, in some implementations, determining the gait parameters can in include integrating the gait parameters at block 413, determining components of the gait phases at block 417, determining gait speed levels at block 421, and combining the gait parameters at the respective speed levels at block 425.

At block 429, the method 400 determines gait symmetries based on the gait parameters determined at block 409. At block 433, the method determine reference gait signatures using the gait parameters determined at 411 and the gait symmetries determines at block 431. At block 437, the method 400 determines treatment effects based on the signatures determined at block 433 and the gait parameters determined at block 409. In some implementations, the patient's gait signature and gait parameters are compared to previous gait signatures to identify changes. For example, the comparison can determine whether treatment of the patient has altered their gait signature. In some implementations, the patient's gait signature and gait parameters can be compared to reference gait signatures and gait parameters to determine similarities. For example, the comparison can determine whether the patient's gait signature and gait parameter are similar to reference gait signatures and gait parameters of different levels of affliction, such as different degrees of osteoarthritis.

FIGS. 5A, 5B, and 5C show example gait parameters in accordance with aspects of the present disclosure. The gait parameters shown in FIGS. 5A, 5B, and 5C can be the same or similar to those previously described above. In some implementations, the gait parameters shown in FIGS. 5A, 5B, and 5C include information derived from the information obtained directly from the sensors of the instrumented footwear (e.g., instrumented footwear 109A, 109B). Additionally, the gate parameters shown in FIGS. 5A, 5B, and 5C can include information directly obtained from the sensors of the instrumented footwear. It is understood that some can user some or all of the gait parameters shown in FIGS. 5A, 5B, and 5C and can include other suitable parameters describing aspects of a user's gait.

FIGS. 6A, 6B, and 6C show heat maps illustrating correlations between gait parameters in accordance with aspects of the present disclosure. FIG. 6A illustrates correlations among gait parameters with a normal (e.g., medium) walking speed group. FIG. 6B illustrates clustering of gait parameters for the normal walking speed group demonstrating that have unique walking signature. FIG. 6C illustrates clustering within the slow, normal, and fast speed group demonstrating that individuals have unique walking signature.

The heatmaps shown in FIGS. 6A, 6B, and 6C illustrate variation in gait parameters using unsupervised hierarchical clustering to group parameter that show trends based on clinical and demographic variables. In the heatmaps, clinical and demographic variables relate to each other (e.g., confound) and similar row variables cluster together. Columns of the heat maps represent individual test routines, wherein individual users (e.g., user 105) cluster with themselves. In some implementations, the gait parameters can include about 45 parameters corresponding to gait report and about 16 parameters corresponding to balance. Between about 5 and about 7 clusters of about 61 raw gait parameters that can be used to identify similar walking trends. For each parameter, the gait analysis system (e.g., gait analysis system 113) can calculate the average for individual users within each speed level. These parameters are in the same category, or are measuring the same motion bilaterally (left vs right foot). For each pair of parameters, the gait analysis system can calculate Spearman correlations within individual speed levels. The Spearman correlations can be used as a distance metric to perform the unsupervised hierarchical clustering to visualize trends. Further, principle components analysis (ordination) reduces variables from 61 dimensions to two dimensions (principle components), while retaining virtually all the variation in the original data. The above analysis can inform asymmetry in walking patterns of users (differences in left vs right foot measurements). Additionally, individual users can be identified through their unique walking signature.

The present disclosure is not to be limited in terms of the particular implementation described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing examples of implementations, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to implementations containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." In addition, where features or aspects of the disclosure are described in terms of Markush groups, those skilled in the art will recognize that the disclosure is also thereby described in terms of any individual member or subgroup of members of the Markush group.

The invention claimed is:

1. A gait analysis system comprising:
instrumented footwear including one or more mobile sensors;
a processor; and
a computer-readable data storage device storing program instructions that, when executed by the processor, control the system to:
determine, using the instrumented footwear, gait information of a user performing a test routine;
determine a plurality of gait parameters based on the gait information, the gait parameters comprising a gait line representing translational movement of a center of pressure (COP) during a stance phase of a stride;
determine correlations between the plurality of gait parameters;
identify a subset of the plurality of gait parameters having an intraclass correlation above a correlation threshold;
determine a gait symmetry of the user based on the subset of gait parameters;
determine a gait signature of the user based on the subset of gait parameters and based on the gait symmetry of the user;
compare the gait signature of the user to a previous gait signature of the user, to a reference gait signature obtained using the subset of gait parameters for afflicted individuals, and to a reference gait signature obtained using the subset of gait parameters for unafflicted individuals to identify a level of change in the user's gait; and
determine a treatment effect on the user's gait based on the identifying the level of change.

2. The gait analysis system of claim 1, wherein the one or more mobile sensors include a plurality of force transducers and a multi-axis accelerometer.

3. The gait analysis system of claim 1, wherein the plurality of gait parameters further comprise: a first peak ground reaction force representing an occurrence of a heel strike component of the stride of the user; a local minimum force representing an occurrence of a terminal stance component of the stride of the user; and a second peak ground reaction force representing an occurrence of a pre-swing component of the stride of the user.

4. The gait analysis system of claim 1, wherein determining the plurality of gait parameters further includes integrating the plurality of gait parameters determined over a distance of the test routine.

5. The gait analysis system of claim 4, wherein determining the plurality of gait parameters further includes determining components of the stride of the user during the test routine.

6. The gait analysis system of claim 5, wherein determining the plurality of gait parameters further includes determining respective gait speed levels of the components of the stride of the user.

7. The gait analysis system of claim 6, wherein determining the respective gait speed levels comprises selecting the respective gait speed levels from a set comprising: a slow speed level, a normal speed level, and a fast speed level.

8. The gait analysis system of claim 7, wherein determining the plurality of gait parameters further includes combining the plurality of gait parameters based on the respective gait speed levels of the plurality of gait parameters.

9. A method for gait analysis using instrumented footwear, the method comprising:
determining gait information of a user performing a test routine based on gait data received from the instrumented footwear;
determining a plurality of gait parameters based on the gait information, the gait parameters comprising a gait line representing translational movement of a center of pressure (COP) during a stance phase of a stride;
determining correlations between the plurality of gait parameters;
identifying a subset of the plurality of gait parameters having an intraclass correlation above a correlation threshold;
determining a gait symmetry of the user based on the subset of gait parameters;
determining a gait signature of the user based on the subset of gait parameters and based on the gait symmetry of the user;
comparing the gait signature of the user to a previous gait signature of the user, to a reference gait signature obtained using the subset of gait parameters for afflicted individuals, and to a reference gait signature obtained using the subset of gait parameters for unafflicted individuals to identify a level of change in the user's gait;
determining a treatment effect on the user's gait based on the identifying the level of change.

10. The method of claim 9, wherein determining the gait information comprises receiving the gait data from a plurality of force transducers and a multi-axis accelerometer included in the instrumented footwear.

11. The method of claim 9, wherein the plurality of gait parameters further include:
a first peak ground reaction force representing an occurrence of a heel strike component of the stride of the user;
a local minimum force representing an occurrence of a terminal stance component of the stride of the user; and
a second peak ground reaction force representing an occurrence of a pre-swing component of the stride of the user.

12. The method of claim 9, wherein determining the plurality of gait parameters further includes integrating the plurality of gait parameters determined over a distance of the test routine.

13. The method of claim 12, wherein determining the plurality of gait parameters further includes determining components of the stride of the user during the test routine.

14. The method of claim 13, wherein determining the plurality of gait parameters further includes determining respective gait speed levels of the components of the stride of the user.

15. The method of claim 14, wherein determining the respective gait speed levels comprises selecting the respective gait speed levels from a set comprising: a slow speed level, a normal speed level, and a fast speed level.

16. The method of claim 15, wherein determining the gait parameters further includes combining the plurality of gait parameters based on the respective gait speed levels of the plurality of gait parameters.

17. A computer program product of a gait analysis system including an instrumented footwear and one or more sensors, the computer program product comprising a computer-readable data storage device storing program instructions that, when executed by a computer processor, cause the gait analysis system to perform operations comprising:
  receiving one or more signals from one or more sensors associated with an instrumented footwear associated with a user performing a test routine, the one or more sensors including at least one of an accelerometer or a pressure sensor;
  determining gait information in response to the one or more signals;
  determining a plurality of gait parameters based on the gait information, the gait parameters comprising a gait line representing translational movement of a center of pressure (COP) during a stance phase of a stride,
  determining correlations between the plurality of gait parameters;
  identifying a subset of the plurality of gait parameters having an intraclass correlation above a correlation threshold;
  determining a gait symmetry of the user based on the subset of gait parameters;
  determining a gait signature of the user based on the subset of gait parameters and based on the gait symmetry of the user;
  comparing the gait signature of the user to a previous gait signature of the user, to a reference gait signature obtained using the subset of gait parameters for afflicted individuals, and to a reference gait signature obtained using the subset of gait parameters for unafflicted individuals to identify a level of change in the user's gait;
  determining a treatment effect on the user's gait based on the identifying the level of change.

18. The computer program product of claim 17, wherein determining the plurality of gait parameters further comprises:
  determining components of the stride of the user during the test routine;
  determining respective gait speed levels of the components of the stride of the user from a set comprising: a slow speed level, a normal speed level, and a fast speed level; and
  combining the plurality of gait parameters based on the respective gait speed levels of the plurality of gait parameters.

19. The gait analysis system of claim 1, wherein the plurality of gait parameters further comprise at least one of a standard deviation of stride gait lines corresponding to the stride, or a mean cycle time.

* * * * *

UNITED STATES PATENT AND TRADEMARK OFFICE
CERTIFICATE OF CORRECTION

PATENT NO. : 12,310,717 B2
APPLICATION NO. : 17/326619
DATED : May 27, 2025
INVENTOR(S) : Wu et al.

Page 1 of 1

It is certified that error appears in the above-identified patent and that said Letters Patent is hereby corrected as shown below:

In the Claims

In Claim 17, Column 13 Line 32, after "stride" replace "," with ";".

Signed and Sealed this
Ninth Day of September, 2025

Coke Morgan Stewart
*Acting Director of the United States Patent and Trademark Office*